US006980114B2

(12) United States Patent
Kleinschmidt

(10) Patent No.: US 6,980,114 B2
(45) Date of Patent: Dec. 27, 2005

(54) REMOTE ACTIVITY CONTROLLER FOR PEOPLE

(75) Inventor: Peter Kleinschmidt, Munich (DE)

(73) Assignee: Siemens Aktiengesellschaft, Munich (DE)

( * ) Notice: Subject to any disclaimer, the term of this patent is extended or adjusted under 35 U.S.C. 154(b) by 118 days.

(21) Appl. No.: 10/681,260

(22) Filed: Oct. 9, 2003

(65) Prior Publication Data

US 2004/0130450 A1    Jul. 8, 2004

(30) Foreign Application Priority Data

Oct. 9, 2002   (DE)   ............................... 102 47 152

(51) Int. Cl.⁷ ............................................. G08B 23/00
(52) U.S. Cl. ............................. 340/573.1; 340/573.17; 706/46; 705/3
(58) Field of Search ........................ 340/539.17, 573.1, 340/825.69, 825.72; 706/45, 62; 600/300, 600/520, 573, 128; 705/1–3

(56) References Cited

U.S. PATENT DOCUMENTS

| | | | | |
|---|---|---|---|---|
| 5,201,034 A | * | 4/1993 | Matsuura et al. | 715/865 |
| 5,375,604 A | * | 12/1994 | Kelly et al. | 600/484 |
| 5,410,471 A | * | 4/1995 | Alyfuku et al. | 600/300 |
| 5,673,691 A | * | 10/1997 | Abrams et al. | 600/300 |
| 5,867,821 A | * | 2/1999 | Ballantyne et al. | 705/2 |
| 5,917,414 A | | 6/1999 | Oppelt et al. | |
| 2003/0208113 A1 | * | 11/2003 | Mault et al. | 600/316 |

FOREIGN PATENT DOCUMENTS

| | | |
|---|---|---|
| DE | 690 30 604 T | 9/1997 |
| DE | 196 31 589 | 2/1998 |
| DE | 693 15 458 T | 4/1998 |
| DE | 19637383 | 4/1998 |
| DE | 699 02 487 T | 12/2002 |
| WO | WO98/15964 | 4/1998 |

* cited by examiner

Primary Examiner—Jeffery Hofsass
Assistant Examiner—Eric Blount
(74) Attorney, Agent, or Firm—Alexander J. Burke

(57) ABSTRACT

A remote activity controller for people is in the form of a portable appliance, including a display apparatus, an internal clock, a user ID code and memory device, and possibly with geographic position recording and with movement and other activity sensors for mobile detection and storage of personal state data for the wearer. Further, a data interface is included via which, when required, a communication link can be set up with contract partners in order to transfer data from the appliance to them, at least at times. In addition, a label communicator is included for detection of information data of measurement or therapy appliances used, including the measurement data determined by these appliances; and also the information about products, such as foodstuffs, medicaments, and network addresses of contract partners or the like, on the basis of labels which are located on or in them or are stored in a label album. Further, a connection for a personal electronic health record is included in which the relevant health data is entered on the basis of a predetermined data scheme, and instantaneous measurement values, consumption values and behavior patterns are added continually to this data, such as weight, blood pressure, temperature, heart rate, test strips and in which other chemical diagnostic values are stored, medicaments consumed, foodstuffs eaten, movement patterns or the like, with timestamps, batch numbers, test equipment types, etc.

29 Claims, 3 Drawing Sheets

REMOTE ACTIVITY CONTROLLER FOR PEOPLE

The present application hereby claims priority under 35 U.S.C. §119 on German patent application number DE 102 47 152.5 filed Oct. 9, 2002, the entire contents of which are hereby incorporated herein by reference.

FIELD OF THE INVENTION

The invention generally relates to a remote activity controller for people. Preferably, it is in the form of a portable appliance with a display apparatus, a clock, an ID code and a memory device, and possibly with position and activity sensors for detection and storage of personal state data for the wearer.

BACKGROUND OF THE INVENTION

Small mobile communication appliances for telecommunications services which can be operated by nonspecialists have already become known in widely different embodiments, and in which context attempts have also already been made to develop universal appliances (in this context see, for example, WO 98/15964). That is to say, attempts have been made to design a control unit such that it is suitable not only for remote control of an appliance, that is to say of a television, radio, computer, telephone or the like, but such that one appliance can be used to operate a large number of widely differing electronic appliances. In this case, as before, the control actions are rather cumbersome and, in particular, the acquisition of data for entering in the appliance is relatively cumbersome and requires a complex input keypad.

One subarea of the detection and storage of personal state data can be provided by an appliance as has been proposed in DE 196 37 383 A1. In this case, a person's state is detected by sensors and is evaluated via an evaluation unit in order to assess the situation relating to this person in comparison to his or her normal daily cycle, taking into account other data, such as the time and the location. If no typical data is available, the person can be reminded by the apparatus, and/or an alarm can be triggered. This arrangement also allows only the detection of the parameters which are monitored from the start by appropriate sensors, but does not allow any communication going beyond this with external third parties, nor does it allow the detection of measurement sensors which are not connected to the system.

SUMMARY OF THE INVENTION

An embodiment of the invention is thus based on an object of refining a remote activity controller such that it can easily detect all possible measurement values using a coherent remote control and dialog concept for services. Further, it can be very simple to operate. Additionally, it can at the same time provide the user with the capability to check a large number of services, in particular health services, and to negotiate contracts relating to them.

In order to achieve this object, a remote activity controller such as this includes, according to an embodiment of the invention, a label communicator for detection of information data of measurement or therapy appliances used, including the measurement data determined by these appliances, and also the information about products, such as foodstuffs, medicaments, and network addresses of contract partners or the like, on the basis of labels which are located on or in them or are stored in a label album, and having a connection for a personal electronic health record in which the relevant health data is entered on the basis of a predetermined data scheme, and instantaneous measurement values, consumption values and behavior patterns are added continually to this data, such as weight, blood pressure, temperature, heart rate, test strips and in which other chemical diagnostic values are stored, medicaments consumed, foodstuffs eaten, movement patterns or the like, with timestamps, batch numbers, test equipment types, etc.

Where labels are referred to in this context, then this is intended to mean not only the normal legible labels that are printed on tags in the form of word and image symbols, but also electronic identification signals, such as transponders with antennas, conductivity patterns or bit patterns on a substrate.

The refinement according to an embodiment of the invention makes it possible in a very simple manner to enter measurement values from any types of appliances directly into the memory of the activity controller. This activity controller not only identifies the display value of the appliance but also a label located on it, with the aid of the label reader. This thus makes it possible to associate the value with that appliance.

For example, the remote activity controller according to an embodiment of the invention uses the label on a balance to identify the fact that this is a balance, so that the determined measurement value must necessarily be the weight. Further characteristics of the balance, such as the type or, for example, the accuracy, may be coded on the label. It could, of course, in a similar way also identify appliances such as a blood pressure gauge, a thermometer, a heart rate gauge or the like, and store the display values in a corresponding manner in the health record. However, this is rather cumbersome for a consistent dialog concept for monitoring and controlling all personal health data, since all the concepts which are based on the patient first of all having to record the data individually, for example via a keypad, or by writing it to a personal health record, would fail from the start.

It cannot be assumed that any significant percentage of the population would be willing and able to carry out such complicated recording processes. However, just touching a test set with the aid of the remote activity controller according to an embodiment of the invention, resulting in the appliance measurement values being automatically transferred to the personal health record is, in practice, not a serious reservation for anyone, which would discourage him or her from using such an activity controller.

In this case, a development of an embodiment of the invention makes it possible to provide for the portable appliance to have only a small number of switching-on, switching-off, operating or selection keys or control wheels for selection of the dialog objects displayed on the display apparatus. Thus, it is invariably possible to dispense with a keypad as in the case of previous appliances. The various response options can be displayed, for example on different lines on the display, in a dialog based on the multiple choice principle, with one of these options being highlighted visually.

The highlighted line is then selected, for example, by use of a dial wheel, up and down keys or by a voice input. For this reason the portable appliance according to an embodiment of the invention for a remote activity controller should preferably include a microphone and a loudspeaker. The confirmation key may in this case be in the form of a multifunctional key, in order that, if necessary, the confirmation can be reversed again in another mode (for example a double click, pushing the button for a long time, or pushing it in the other direction).

It is particularly advantageous for the remote activity controller to include a memory for the personal electronic health record, so that at least the most important parts of the health record are integrated directly in the remote controller and are not just coupled to it via a data radio interface.

The remote activity controller according to an embodiment of the invention may in this case have an (external) communication module to a station which is not mobile and which may also have interfaces, in the form of radio links, for a network such as the Internet which can be used universally. In this case, if necessary, an entire mobile radio part can be integrated.

In order to make it possible to display the determined and stored data not only in a simple manner for the user on a display, but also to make it easier for the user to make deliberate selections for passing on such data. It is possible, in one refinement of an embodiment of the invention, for a decoder to be provided for interpretation of the determined time-dependent data and, possibly, for compression and/or for masking out various parts from the decoded recording. As such, parts such as these can be made available, for example via an interface, for sending via the data network and for entry in the health record.

According to a further feature of an embodiment of the present invention, the remote activity controller is intended to include tools, in particular a printer, for producing external labels. These labels that are produced and which represent some values of the user or service provider addresses coded in this way, may, for example, be applied to objects, for example for the purpose of storage outside the appliance. By way of example, a paper-based label album can be used as a directory or repository, in which the machine-legible tags are stuck on or are inserted.

The data banks that are normally used in mobile devices and contain stored addresses, their control and display by means of a built-in display, the data interchange by radio or infrared, as well as the details of Internet addresses already achieve this object, in principle. However, all known solutions are so complex to use and, furthermore, are frequently incompatible or difficult to configure, so that this situation is preventing more widespread use of electronic services.

The essential feature of the embodiment of a remote activity controller according to an embodiment of the invention is that the entire wide range of details of overview information, which is offered in a parallel form, for a physically represented album with informative icons and company logos, as well as having a direct manipulation capability (writing, deletion) of the addresses, can be looked through with lightning speed. This cannot be provided at this speed and with this clarity by small displays and acoustic signaling devices. Some service providers may be able to use this refinement of the remote activity controller according to an embodiment of the invention to offer their services in the form of prefabricated tags which can be stuck in and which, by virtue of their graphical configuration, can be recognized again well by eye, may include printed instructions, and may have dedicated comments added to them by the user. These tags can be read by the scanner device or the label reader, and the graphics and text information can also be displayed on the display. The user's management is made much easier by the fact that addresses follow the same control philosophy exactly in the same way as the scanning of labels applied to goods and appliances.

In this case, optical scanners (for example bar code readers) are used in particular as a reading apparatus for the label communicator, and normal printers are used as a corresponding writing apparatus, by means of which bar codes can also be printed, in addition to plain text. In addition to optical bar codes, conductivity patterns, chips with contacts or transponders with antennas and internal bit patterns can also be used, as has already been mentioned further above. In practice, label readers will be designed to be multimodal and to be able to cope with two or more signal types at the same time.

A remote activity controller according to an embodiment of the invention may, furthermore, also if required be provided with further tools for activity monitoring, such as an acceleration sensor which records the movement of the wearer, and with a geographical position finder, for example with GPS detectors or with reception of landmarks whose locations are known, or else with a camera, and with the decoder preferably having image recognition components. In this case, it is also within the scope of an embodiment of the invention for the activity controller according to an embodiment of the invention to include a gas sensor or smoke sensor, and for the decoder to have gas, gas mixture or smoke identification components.

The remote activity controller may be arranged on an armband on its own or in conjunction with other appliances, for example being integrated in a clock or a mobile telephone or the like. Alternatively, it may be at least partially implanted in the body of the wearer, may be stuck on to the body, or may be incorporated in the clothing of the wearer. At least partial incorporation in a hearing aid or in a finger ring is also feasible in this context.

In addition to the embodiment of the remote activity controller as an integral portable appliance, it is also possible to provide a refinement in which the remote activity controller includes two or more interacting appliance units. In this case, of course, as is already in principle known, authentication devices should be integrated. This should bew done in order to ensure authentication of the wearer, and hence secure personal association of the data record and passing on of data by means, for example, of a PIN, password, chip, biometric features or the like.

Finally, it is also within the scope of an embodiment of the invention for the remote activity controller to include a memory, which can possibly be operated via a data interface, for electronic contracts relating to services based on the data, or means for accessing such contracts, as well as the names and access addresses of contract partners, preferably combined in the form of labels. In this case, the contract partner can send "soft labels" to the appliance, and these can be printed out by the user and can be applied to goods or appliances, and can be entered in the label album. Furthermore, it is possible to provide implemented rules to determine whether and in what circumstances data or parts of such data may be passed onto third parties in an open form or in a scrambled form, for which purpose a further electronic data interface can be implemented in the appliance, for communication with external third parties.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein.

DETAILED DESCRIPTION OF THE PREFERRED EMBODIMENTS

Figure 1:
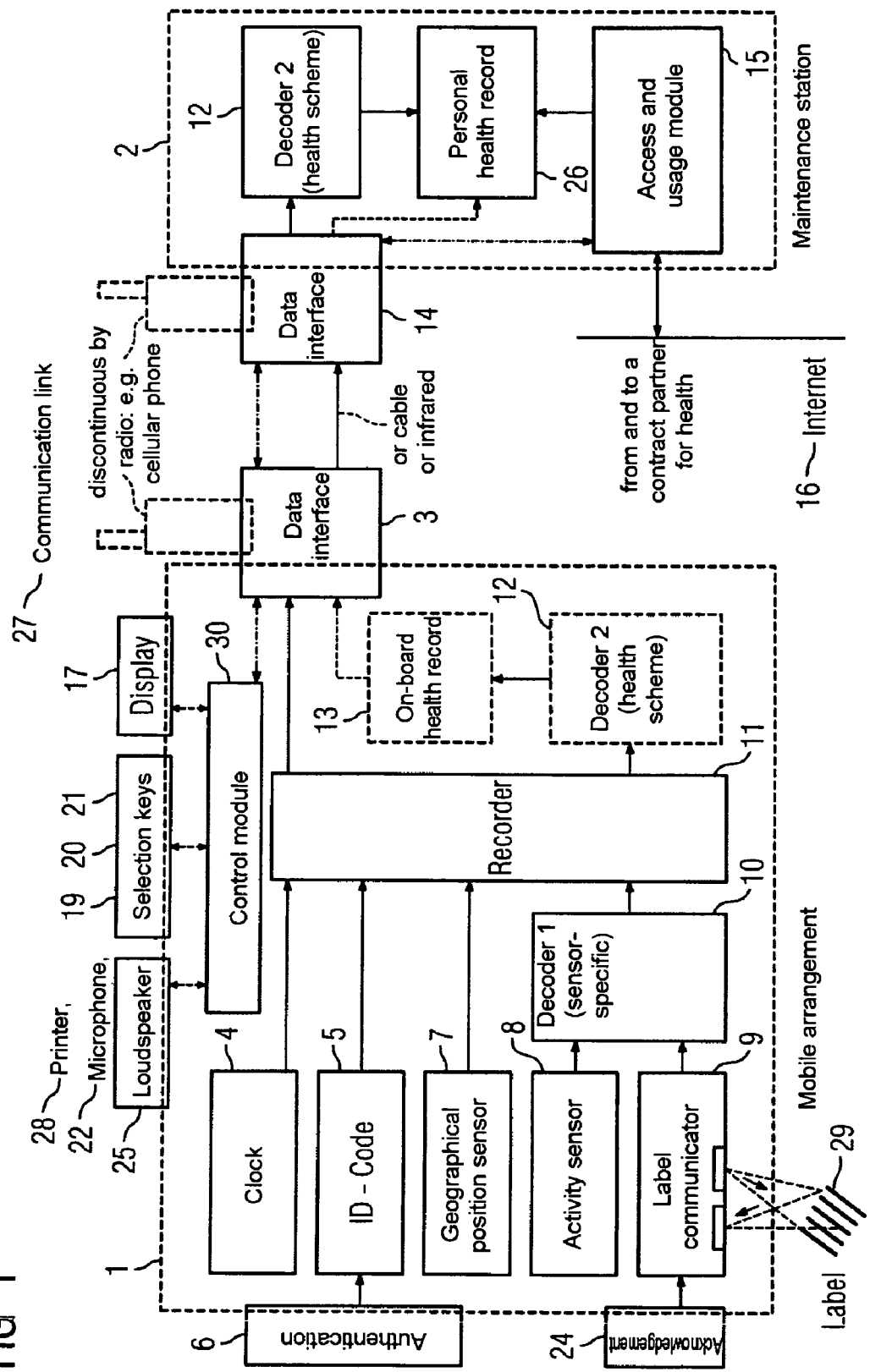
FIG. 1 shows a block diagram of the configuration of a remote activity controller according to an embodiment of the invention.

The remote activity controller shown in FIG. 1 has a mobile appliance 1 as a personal recording part, and has a personal contract management and maintenance station 2. In this case this could, if required, also be integrated in the mobile appliance 1, instead of using the connection as illustrated via a data interface 3. In addition to an internal clock for producing the time markers 4, a user ID code 5 in conjunction with an authentication device 6, a position sensor 7 and an activity sensor 8.

The mobile appliance has, as a key component, a label reader 9 which may, in turn, have an associated label printer 28. The activity sensor 8 and the label reader 9 are connected to a sensor-specific decoder 10. All the addressed appliances are followed by a recorder 11. The recorder 11 may either be additionally connected via the interface 3 to a personal electronic health record 26, or else an electronic on-board health record 13 such as this may also be included in the mobile appliance 1.

In both cases, a decoder-2 12 ensures that the data is reduced to what is medically necessary and is entered at the correct location in the layout of the health record. The decoder-2 receives its layout information by use of templates which are made available to the user by his or her health service partners (see the parallel application to e-commerce with health data).

In order to make it possible to use the data correctly, the personal maintenance station has an access and usage module 15 for the health record, although this will not be described in any further detail in this patent specification. The components of this module are used to process and filter the data in the health record, to process the data for commercial traffic in accordance with the contract with health service partners and brokers for these services, and to make the data secure. Details relating to this are included in the parallel application relating to e-commerce with health data.

The remote activity controller has a passive mode in which it is used purely passively for acquisition recording and storage of data. There is no need for a data link to the maintenance station or to health service providers for this purpose. This is done at some other better point in time. In contrast to this, an active mode is desired for dialog purposes, with a bidirectional data link 3, 14, to the maintenance station, and from there or directly to the health service providers via Internet 16. The dialog instructions and multiple choice questions are passed via the backward channel to the control module 30, and form there to the control outputs 17 and 25. The backward channel may also be used to maintain and to calibrate the appliances remotely. For situations such as these, it is envisaged that the label reader 9 will be designed to be bidirectional, and that the labels can likewise receive signals. This is the situation, for example, when a label is in the form of an infrared interface or a radio interface.

Figure 2:
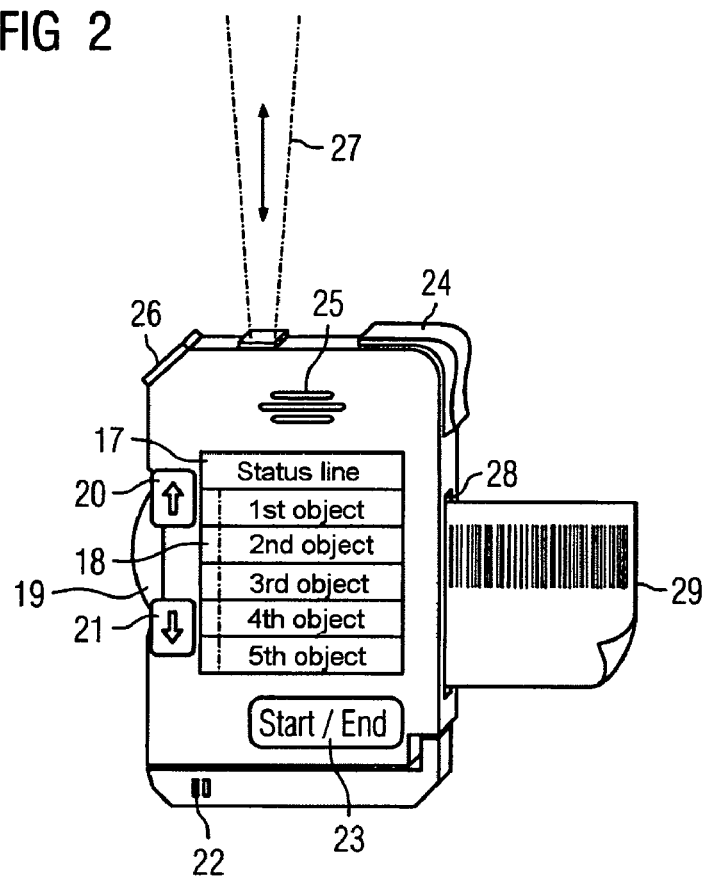
FIGS. 2 to 4 show an exemplary embodiment of the configuration of an activity controller which has only a small number of control elements, with FIG. 3 and FIG. 4 illustrating different modes of use.

FIG. 2 shows one exemplary embodiment of a portable appliance for a remote activity controller according to an embodiment of the invention. The appliance in this case has a display 17 for highlighting a dialog object 18 which is displayed on it, as well as a control wheel 19 and up and down keys 20, 21 as tools for selection of the dialog object. In addition to a microphone 22, which can also, for example, be folded out, a start and end control switch 23 and a switch 24 as a tool for operating a selection by clicking for a correspondingly longer time or by clicking more than once, the illustrated exemplary embodiment has a separate loudspeaker 25 as well as an optical scanner 26, and an IR/radio interface for the communication link 27.

Figure 3:
Figure 4:
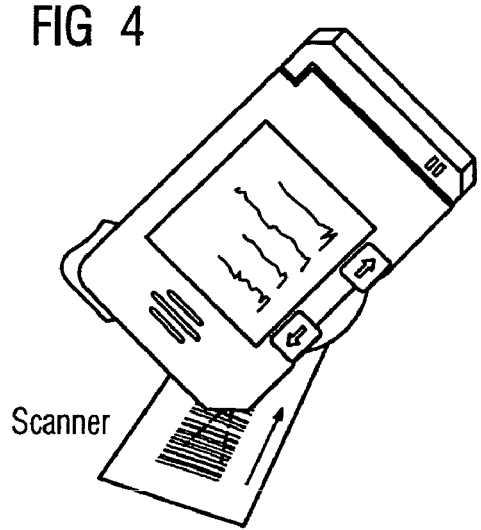
Figure 5:
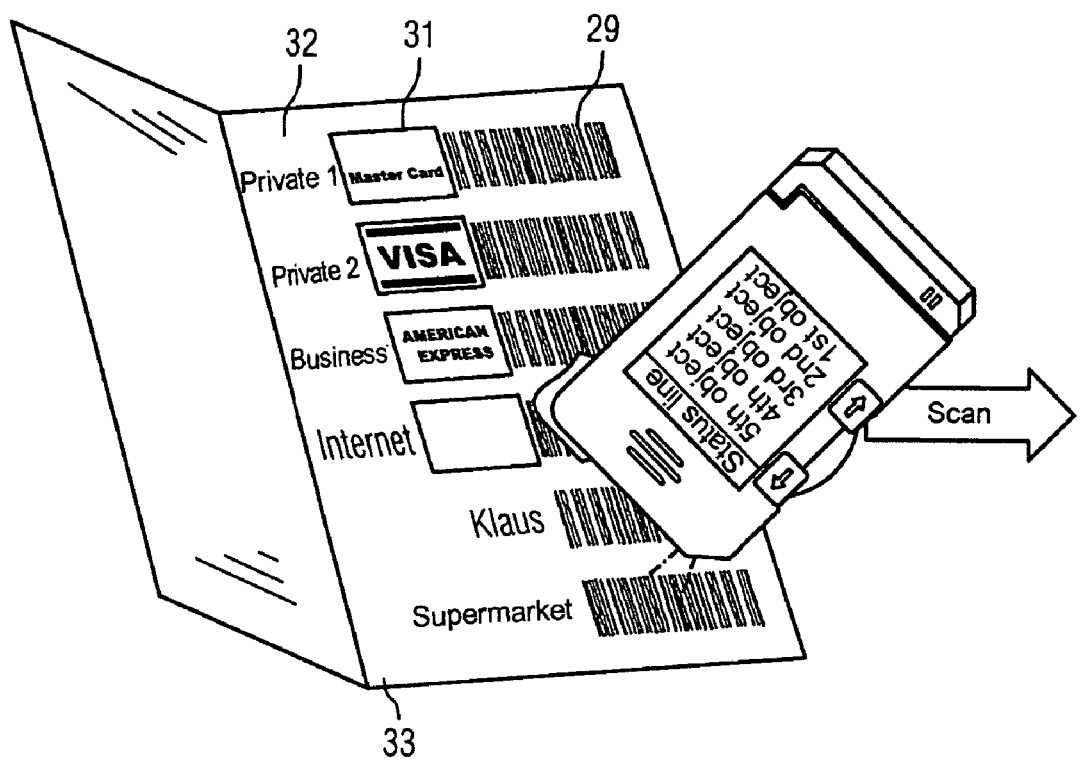
FIG. 5 shows a schematic detail from a label album for use in conjunction with a remote activity controller according to an embodiment of the invention.

FIGS. 3 and 4 in this case show how the appliance can be used as a label reader or as a scanner. An output, which is associated with a printer, for labels 29 which are produced in the appliance is shown at 28 (see FIG. 2) and may, for example, be stuck onto external appliances, or may be used in conjunction with a paper-based label album as shown in FIG. 5. This shows a series of labels which have been stuck on or have been inserted into corresponding pages, from which the user can scan in the appropriate contract partner simply by placing the remote activity controller according to the invention on it, with the labels for this contract partner then at the same time being displayed on the display, in order that a dialog can subsequently be set up with the appropriate partner by radio. The scanning process activates the service for which the entered information data or subsequent information data is intended, for example credit cards 31, information services, health services, in which case these may be telecommunications services, advice services, doctors, restaurants, etc, as well as deliver addresses, authorizations 32, etc.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A remote activity controller employed by a user, comprising:

a display apparatus;

an internal clock;

a user ID code and memory device;

a data interface for establishing a communication link with at least one contract partner having a predetermined relationship with the user in order to transfer data from at least one appliance to the at least one contact partners; and a label communicator for detection of information data associated with a label of at least one of measurement and therapy appliances, wherein the information data comprises the measurement data determined by at least one appliance, information about products and network addresses of contract partners, wherein the label is located at least one of on the appliance, in the appliance and stored in a label album, and means for creating a personal electronic health record in which relevant health data is entered on the basis of a predetermined data scheme, and instantaneous measurement values, consumption values and behavior patterns are added continually to the relevant health data and are stored.

2. The remote activity controller as claimed in claim 1, wherein the label communicator includes at least one of optical, magnetic, electrical and mechanical scanners to at least one of read the information coded on a substrate on the labels,
read the electromagnetic signal transmitted from radio labels and coded with the information, and
read acoustic signals and the information contained in it.

3. The remote activity controller as claimed in claim 2, wherein the data interface for the communication link to contract partners allows data to be transported from the contract partners to the appliance, and wherein this information is used in order to transmit information via the label communicator to configure remote devices.

4. The remote activity controller as claimed in claim 1, wherein the remote activity controller includes at least one of a control wheel and at least one key for at least one of switching-on, switching-off, operating and selection for selection of the dialog object which is indicated on the display apparatus.

5. The remote activity controller as claimed in claim 1, wherein the data interface also allows data to be transported from the contract partners to the appliance for the communication link to contact partners, and wherein the data is used via a control module in order to carry out dialogs with the user, via the display.

6. The remote activity controller as claimed in claim 1, further comprising a memory and a decoder for the personal electronic health record, and data is stored therein on the basis of the scheme, and is provided at the data interface.

7. The remote activity controller as claimed in claim 1, further comprises an Internet-compatible communication module in order to provide the communication link, the communication module including access to the Internet without the use of wires via at least one of a mobile radio and infrared.

8. The remote activity controller as claimed in claim 1, comprising:

a decoder for at least one of interpretation of time-dependent data, compression of data, and selecting a predetermined portion from the decoded data.

9. The remote activity controller as claimed in claim 1, further comprising a tool for producing external labels.

10. The remote activity controller as claimed in claim 1, comprising at least one of the following for geographical position recording, including a GPS module
a receiving device for landmarks of a known geographic position, and
a system in which network operator data associated with time-related use of the local radio cell is obtained and is correlated with the appliance timer markers.

11. The remote activity controller as claimed in claim 1, further comprising a microphone and a loudspeaker, used to assist the dialog with the user.

12. The remote activity controller as claimed in claim 1, further comprising a camera with a decoder including image recognition components.

13. The remote activity controller as claimed in claim 1, further comprising an optical scanner for optical codes.

14. The remote activity controller as claimed in claim 1, further comprising a gas sensor and smoke sensor, and a decoder having at least one of gas, gas mixture and smoke identification components.

15. The remote activity controller as claimed in claim 1, wherein the remote activity controller is arranged on an armband.

16. The remote activity controller as claimed in clam 1, wherein the remote activity controller is at least one of at least partially implanted in the body of the wearer, is stuck on to the body, and is incorporated in clothing of the wearer.

17. The remote activity controller as claimed in claim 1, wherein the remote activity controller is at least partially incorporated in at least one of a hearing aid and a finger ring.

18. The remote activity controller as claimed in claim 1, wherein the remote activity controller comprises at least two interacting appliance units.

19. The remote activity controller as claimed in claim 1, further comprising at least one authentication device.

20. The remote activity controller as claimed in claim 1, further comprising:

a memory, drivable via at least one of a data interface for electronic orders, and
means for accessing at least one of orders, names of contact partners and addresses of contract partners.

21. The remote activity controller as claimed in claim 20, wherein predetermined rules select circumstances wherein at least one of data and parts of such data, are passable onto third parties in at least one of an open form and in a scrambled form.

22. The remote activity controller as claimed in claim 1, wherein the label communicator transmits a signal, which is received by a transponder label and is sent back having been modified on the basis of the information on the label and is read.

23. The remote activity controller as claimed in claim 22, wherein the the transponder label receives the signal transmitted from the label communicator and passes the modified signal to the associated appliance.

24. The remote activity controller as claimed in claim 20, comprising an electronic data interface for communication with external third parties.

25. The remote activity controller as claimed in claim 21, comprising an electronic data interface for communication with external third parties.

26. The remote activity controller as claimed in claim 1, wherein the remote activity controller is portable.

27. The remote activity controller as claimed in claim 1, comprising means for recording geographic position and including movement and other activity sensors for mobile detection and storage of personal state data for the wearer.

28. The remote activity controller as claimed in claim 15, wherein the remote activity controller is arranged on an armband in conjunction with at least one other appliance including at least one of a clock, an appropriately configured mobile telephone, and a PDA.

29. A remote activity controller, comprising:

a data interface for establishing a communication link with contract partners, to transfer data therebetween; and
a label communicator for detection of information data of at least one of measurement and therapy appliances associated with a label stored in a label album, wherein the information data includes measurement data, information about products and network addresses of contract partners, and including a connection for a personal electronic health record in which relevant health data is entered on the basis of a predetermined data scheme, and instantaneous measurement values, consumption values and behavior patterns are added continually to the relevant health data.

* * * * *